United States Patent [19]

Keramaty et al.

[11] Patent Number: 4,580,898
[45] Date of Patent: Apr. 8, 1986

[54] ANALYTICAL SYSTEM

[75] Inventors: Hamid Keramaty, Lexington, Mass.; Gary C. Lu, Grenada Hills, Calif.; Larry A. Nelson, Spokane, Wash.

[73] Assignee: Allied Corporation, Morristown, N.J.

[21] Appl. No.: 615,645

[22] Filed: May 31, 1984

[51] Int. Cl.⁴ .............................................. G01N 21/07
[52] U.S. Cl. .................................... 356/246; 356/427; 422/64
[58] Field of Search ......... 356/246, 427, 440; 422/64, 72; 436/45

[56] References Cited

U.S. PATENT DOCUMENTS

| | | | |
|---|---|---|---|
| 3,586,484 | 6/1971 | Anderson | 23/230 |
| 3,759,666 | 9/1973 | Hill | 23/230 |
| 3,798,459 | 3/1974 | Anderson | 250/218 |
| 3,813,031 | 5/1974 | Anderson | 233/26 |
| 3,873,217 | 3/1975 | Anderson | 356/246 |
| 3,899,296 | 8/1975 | Mailen | 23/259 |
| 4,123,173 | 10/1978 | Bullock | 356/246 |
| 4,226,531 | 10/1980 | Tiffany | 356/246 |
| 4,314,970 | 2/1982 | Stein et al. | 356/246 X |
| 4,373,812 | 2/1983 | Stein | 356/246 |

Primary Examiner—Vincent P. McGraw
Assistant Examiner—Robert D. V. Thompson, III
Attorney, Agent, or Firm—Lowell H. McCarter

[57] ABSTRACT

A multicuvette rotor for use in a centrifugal analyzer defines a circumferential array of elongated radially extending cuvettes. The rotor includes a one-piece body member of material that is transparent at analytical wavelengths and has a planar upper surface and defines a circumferential array of elongated cuvette recesses, and a one-piece cover member of similarly transparent material that has a planar lower surface parallel to the planar upper surface of the body member. A continuous seal extends around each cuvette recess between the planar upper and lower surfaces to define the circumferential array of analytical cuvettes. Each elongated cuvette defines a first chamber for receiving a first constituent with a loading port in the cover member through which the first constituent is introduced into the first chamber region, a second chamber region for receiving a second constituent with a loading port in the cover member through which the second constituent is introduced into the second chamber region, divider structure between the first and second chamber regions provides a transfer passage between the first and second chamber regions through which the first constituent may be flowed into the second chamber region for forming a reaction product with the second constituent, and structure defining an analysis region adjacent the radially outer wall of the cuvette where the resulting reaction product is subjected to analysis. Extending along the top of each sidewall of each cuvette between the loading ports of the first and second chamber regions is barrier structure that fills the junction between the cover and body members so that there is no capillary channel at that junction and premature mixing of the constituents due to wicking movement of a constituent stored in one of the chamber regions to the other chamber region along that junction is inhibited.

12 Claims, 10 Drawing Figures

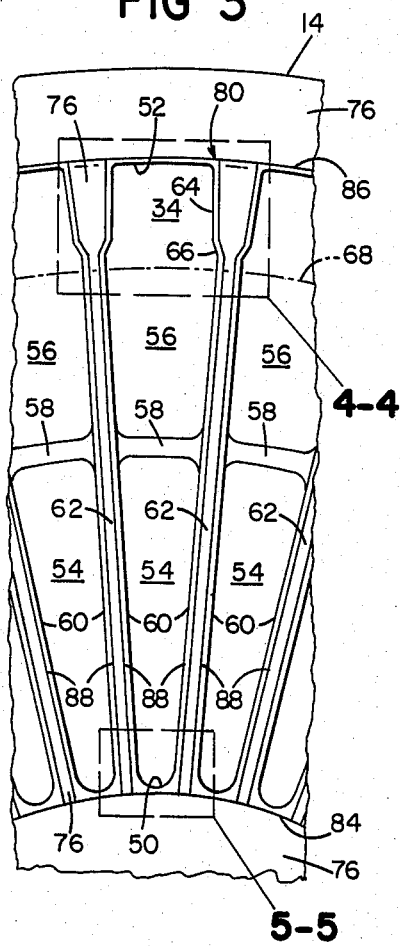
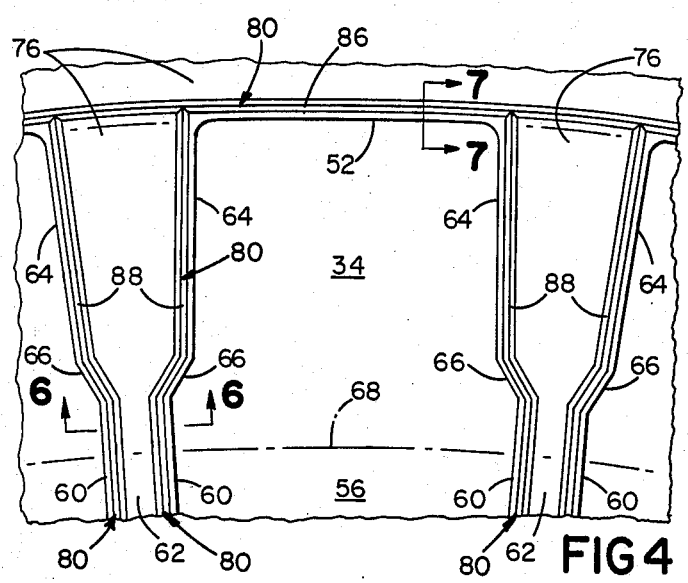
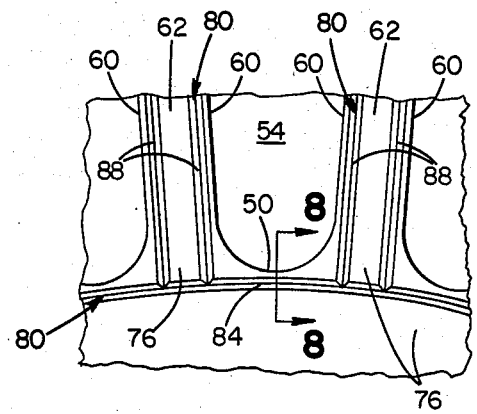
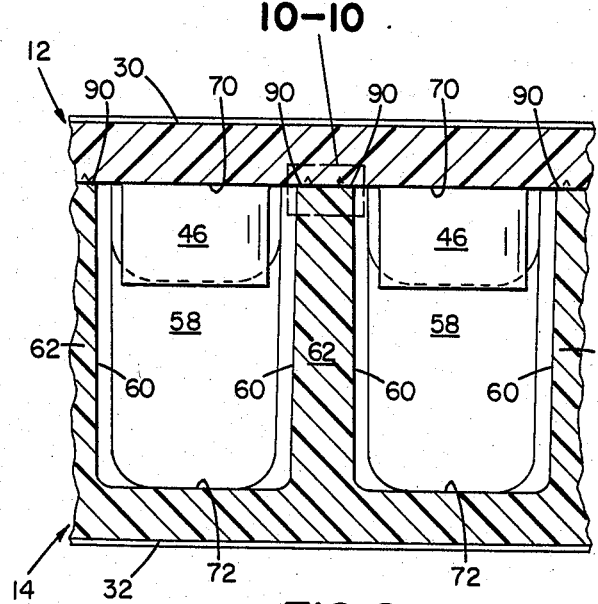
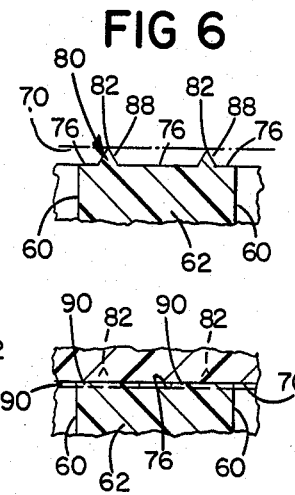
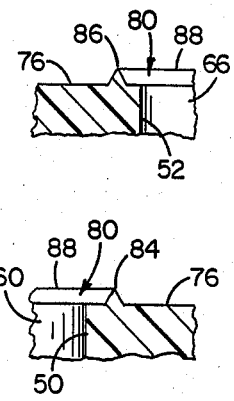

ANALYTICAL SYSTEM

This invention relates to analytical systems, and more particularly to multicuvette rotors for use in centrifugal analyzer systems.

Centrifugal chemical analysis systems employ a cuvette rotor assembly that defines a circumferential array of spaced elongated radially extending cuvettes, each of which has two chambers for initially storing reagent materials separately and then transferring reagent material from one chamber to another for mixing and reaction, and subsequent analysis of the reaction in the analysis region by the cooperating analyzer. Cuvette rotor assemblies of this type are disclosed in Tiffany et al. U.S. Pat. No. 4,226,531 and Stein et al. U.S. Pat. No. 4,373,812. In use of such rotors, sample to be analyzed (frequently with supplemental reagent material) is introduced through a loading port into one chamber and a second reagent material is introduced through a second loading port into the second chamber. The rotors disclosed in the above mentioned patents have twenty cuvettes that are loaded successively with automated loading equipment, small quantities of sample plus optional quantities of diluent and second reagent (volumes typically in the range of 2–100 microliters) being pipetted through loading ports into first chambers, and reagents in quantities up to 200 microliters being pipetted through loading ports into second chambers. The loaded cuvette rotor is then transferred to an analyzer for photometric, light scatter and/or fluorescence analysis During the analysis sequence, the rotor usually is driven at a preliminary fast speed in the vicinity of 3000–5000 rpm in which the reactant in each inner chamber flows over divider structure and mixes with the reactant in the outer chamber, and then the rotor is driven at speeds in the vicinity of 500–1000 rpm during a measurement interval.

Numerous analytical tests are performed with such analyzers including, for example, glucose, creatinine, CPK, SGOT, triglyceride, and enzyme immunoassays. It has been found that there is an unacceptable tendency for reagent material to spontaneously move or "wick" along the upper surface of the cuvette resulting in premature mixing of reagents between the two chamber compartments, such mixing occurring in the case of some tests in less than one minute after loading, while the loading sequence may take five minutes or more. For example, a drop of sample or reagent material (of several microliters in size) may adhere to a cuvette sidewall and transfer from there along a capillary channel between the top of the cuvette sidewall and the cover into the chamber from which it is supposed to be excluded until the reaction is initiated by a centrifuging action. This problem is particularly significant with reagent materials that have high wettability characteristics such as reagents used in enzyme immunoassays, for example.

In accordance with one aspect of the invention, there is provided a multicuvette rotor for use in a centrifugal analyzer that defines a circumferential array of elongated radially extending cuvettes. The rotor includes a one-piece body member of material that is transparent at analytical wavelengths and that has a planar upper surface and that defines a circumferential array of elongated cuvette recesses, and a one-piece cover member of similarly transparent material that has a planar lower surface parallel to the planar upper surface of the body member. A continuous seal extends around each cuvette recess between the planar upper and lower surfaces to define the circumferential array of analytical cuvettes. Each elongated cuvette defines a first chamber for receiving a first constituent with a loading port in the cover member through which the first constituent is introduced into the first chamber region, a second chamber region for receiving a second constituent with a loading port in the cover member through which the second constituent is introduced into the second chamber region, divider structure between the first and second chamber regions provides a transfer passage between the first and second chamber regions through which the first constituent may be flowed into the second chamber region for forming a reaction product with the second constituent, and structure defining an analysis region adjacent the radially outer wall of the cuvette where the resulting reaction product is subjected to analysis. Extending along the top of each sidewall of each cuvette between the loading ports of the first and second chamber regions is barrier structure that fills the junction between the cover and body members so that there is no capillary channel at that junction and premature mixing of the constituents due to wicking movement of a constituent stored in one of the chamber regions to the other chamber region along that junction is inhibited.

In preferred embodiments, the barrier structure is integral with the continuous cuvette seal and is formed of melted and flattened energy director ridge material, the barrier ridge portion, before melting and flattening, being spaced from the edge of the adjacent cuvette side wall substantially the same distance as its height. The energy director ridges are located such that, after welding, the portion of the energy direction which has "melted" fills the void between the top cover and the top of the cuvette sidewall and a smooth, radiused junction is formed between the two components of the rotor assembly. While the energy director ridge seal and barrier structures may be formed on either the body member or the cover member, or partly on each, preferably the barrier and seal structures are integral with the body member. By properly positioning the energy director ridges on the rotor body and by using two ridges along the top surface of each sidewall defining web, the required amount of energy director ridge material is reduced and less uncertainty in the finished (welded) rotor optical path length between cuvettes and between rotors results.

In a particular embodiment, the rotor assembly has a diameter of about ten centimeters and an overall height of about one centimeter, the cover member is a flat circular disc that has an optical window region, an outer circumferential array of loading ports, an inner circumferential array of loading ports, and a substantially "D" shaped central opening; and the body member has a flat upper surface, an optical window region formed in its lower surface that is aligned with the optical window region of the cover member and a circumferential array of thirty-nine individual cuvette recesses. Each cuvette recess of that rotor has a length of about three centimeters, the chamber sidewalls diverge at an angle of about nine degrees from the center of the rotor, and the analytical region (defined by the pair of opposed optical windows adjacent the outer periphery of the rotor disc) has parallel side walls. That rotor embodiment includes triangular energy director ridge portions that have a base width of about 0.1 millimeter, a height of about 0.1 millimeter, and are set back about 0.1 millimeter from and extend parallel to the adjacent top edge of the cuvette side wall. The web thickness between each cuvette is small—less than 0.3 centimeter, and a pair of parallel energy director ridges are integrally formed on the planar upper surface of each such web.

In centrifugal analyzer rotors in accordance with the invention, spontaneous mixing of sample and reagent due to wicking along the junction between cover and cuvette side walls is significantly impeded without increase in the size of the rotor and with significant increase in the number of cuvettes in the rotor assembly.

Other features and advantages of the invention will be seen as the following description of a particular embodiment progresses, in conjunction with the drawings, in which:

FIG. 3 is an enlarged view of a portion of the body member of the rotor assembly shown in FIG. 1;

FIGS. 4 and 5 are still further enlarged views of portions of the body member indicated at 4—4 and 5—5 in FIG. 3;

FIG. 6 is a sectional view taken along the line 6—6 of FIG. 4;

FIG. 7 is a sectional view taken along the line 7—7 of FIG. 4;

FIG. 8 is a sectional view taken along the line 8—8 of FIG. 5;

FIG. 9 is an enlarged sectional view taken along the line 9—9 of FIG. 1; and

FIG. 10 is a further enlarged view of the portion indicated at 10—10 in FIG. 9.

DESCRIPTION OF PARTICULAR EMBODIMENT

Figure 1:
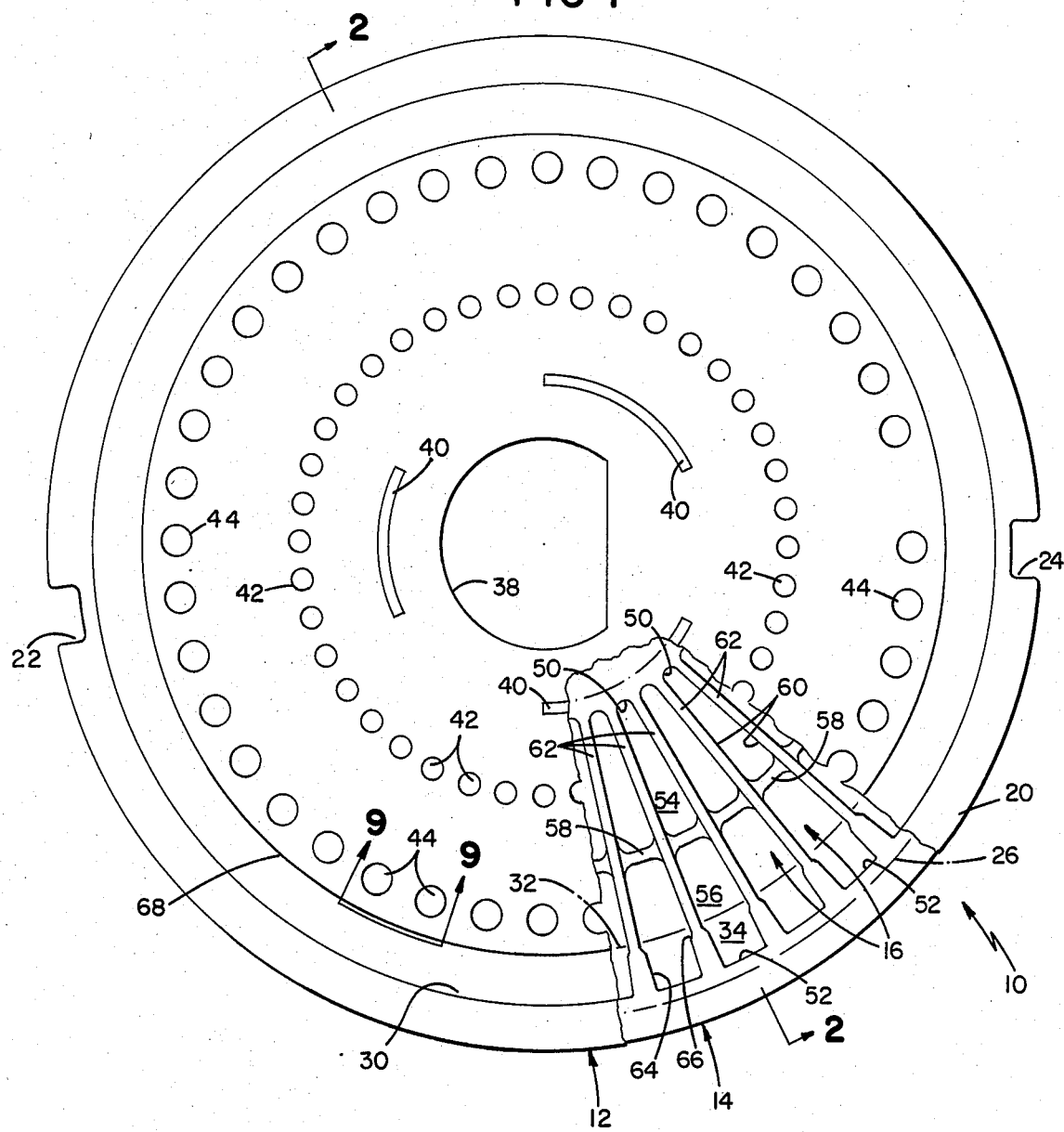
FIG. 1 is a top plan view (with portions broken away) of a multicuvette rotor assembly in accordance with the invention.
Figure 2:
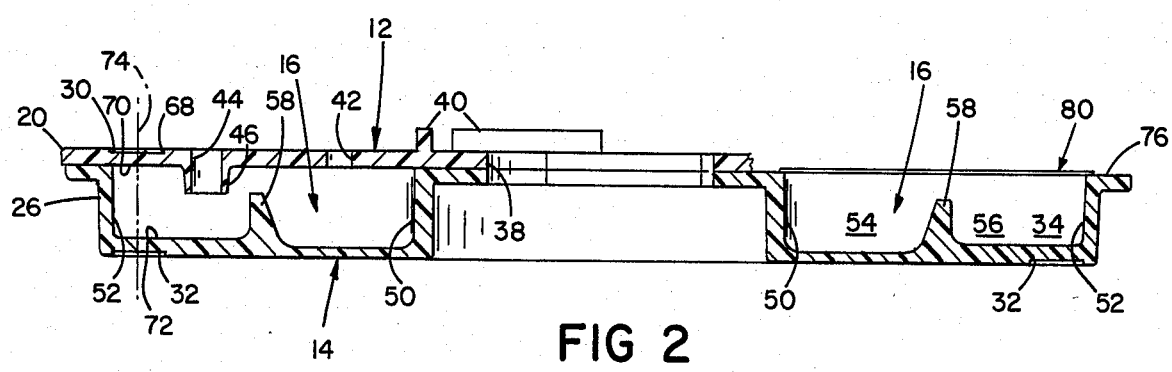
FIG. 2 is a sectional view taken along the line 2—2 of the rotor assembly shown in FIG. 1.

With reference to FIGS. 1 and 2, rotor assembly 10 has a diameter of about ten centimeters and an overall height of about 1 ¼ centimeters, and is formed of an injection-molded acrylic cover member 12 and an injection-molded acrylic body member 14 that are ultrasonically welded together, the body and cover members having appropriate transparency, chemical resistance, and optical characteristics for photometric analysis. Rotor assembly 10 defines a circumferential array of thirty-nine individual analysis cuvettes 16 (plus a reference region of similar configuration) and has circumferential flange structure 20 at its periphery in which are formed alignment recesses 22, 24, and with a continuous circumferential surface 26 below flange 20 in which is located a series of optical end windows, one for each cuvette 16. Optical window channel recess 30 (about ½ centimeter wide with its inner edge at about four centimeters radius) is formed in the upper surface of rotor assembly 10, and a corresponding continuous annular optical window channel recess 32 is formed in the lower surface of rotor 10, channels 30, 32 being aligned and defining cuvette analysis regions 34 therebetween.

Formed in cover member 12 (as indicated in FIG. 1) are a substantially D-shaped central opening 38, a series of three arcuate spacer ribs 40, a circumferential array of first loading ports 42, a second circumferential array of second loading ports 44 with depending tubular extensions 46, and annular recessed optical window channel 30 outwardly of ports 44 and adjacent rim 20.

The thirty-nine analysis cuvettes 16 are of the same configuration, each cuvette 16 having a length of about three centimeters between cylindrical inner wall surface 50 and planar outer wall 52 surface that has an optical surface finish of better than three microinches and which defines the inner surface of optical window 28. Each cuvette 16 has an inner chamber portion 54 (which is loaded through its port 42) and an outer chamber portion 56 (which is loaded through its port 44) that are separated by divider ramp structure 58. The surfaces 60 of each cuvette that define the side walls of chambers 54 and 56 are formed by solid webs 62 that are about one millimeter thick and diverge at an angle of nine degrees. As may be seen with reference to FIGS. 1-4, the analysis region 34 of each cuvette is bounded by parallel side wall surfaces 64 (spaced about 0.5 centimeter apart) adjacent outer wall 52, and short transition wall surfaces 66 (inclined at an angle of about 30 degrees) connect diverging side wall surfaces 60 of chambers 56 (where they are spaced about 5.5 millimeters apart) and side wall surfaces 64 of analysis regions 34.

The two aligned optical window channels 30, 32 are each about ½ centimeter wide, with the inner edges 68 of channels 30, 32 located slightly radially inwardly of transition surfaces 66 of cuvette 16. The upper and lower surfaces 70, 72 in analysis region 34 have optical finishes of better than three microinches (as have surfaces 30, 32 and 52) and are spaced about ¾ centimeter apart to provide an optical path 74 (FIG. 2) of about ¾ centimeter length in each analysis region 34.

Further details of body member 14 may be seen with reference to FIGS. 2-7. Member 14 has planar upper surface 76 on which is formed an interconnected array of energy director ridges 80 so that there is continuous ridge structure that extends about the perimeter of each individual cuvette 34, as indicated in FIGS. 1-3. Each energy director ridge 80 extends parallel to and is set back about 0.1 millimeter from the edge of the adjacent cuvette wall sections 50, 52, 60, 64, and 66 and is of triangular cross-sectional configuration. With reference to FIGS. 6-8, each ridge 80 has a base width of about 0.1 millimeter and a peak 82 that has a height of about 0.1 millimeter; and the energy director ridges 80 include inner ring section 84, outer ring section 86, and sidewall sections 88.

In sealing cover 12 to body 14, cover 12 is placed on the upper surface 76 of body 14 and then ultrasonically welded to body 14 with a horn pressure of about 60 psi and application of twenty kilohertz energy for about one second. That ultrasonic energy and pressure melts and flattens the energy director ridges 80 as indicated at 90 in FIGS. 9 and 10 with ridge material flowing to the sidewall of the cuvette, and creating a peripheral seal of melted plastic material (as indicated at 90 in FIGS. 9 and 10) about each cuvette 16. The flow of melted plastic material 90 along surface 76 to side wall 60 (50, 52, 64, 66) smoothly fills the gap between cover surface 70 and body surface 76 adjacent cuvette side wall portions 50, 52, 60, 64, 66. Such a gap in prior rotors has been found to induce rapid capillary "wicking" action that transfers any reagent that contacts it from one compartment 54 or 56 to the other compartment with resultant premature mixing, and the smooth joinings of surfaces 70 and 76 by the flowed, flattened melted energy director ridge structures 80 inhibit spontaneous premixing of reagent materials.

In use of this rotor embodiment, a selected sample volume in the range of 2-20 microliters (optionally with an additional volume of supplemental reagent material or diluent) is dispensed into chamber 54 and a selected reagent volume in the range of 150-200 microliters is dispensed into chamber 56 depending on the particular test involved. As indicated above, potential wicking action is inhibited by the melted structures 90 of energy director ridges 80 such that spontaneous mixing of reagents due to such capillary wicking action between the two chambers of the cuvette is essentially prevented.

After some or all of the thirty-nine cuvettes 16 of rotor 10 have been loaded, the rotor is transferred to an analyzer for incubation (if necessary), centrifugal acceleration to provide transfer of the sample (and reagent) from chamber 54 to analysis chamber 34 and mixing. The rotor is then braked and then accelerated again to about 600 rpm for photometric analysis. The barrier structures 90 of melted ridges 80 retard spontaneous 'wicking' and 'creep' type flows of reagent in either direction from one chamber to the other while not interfering with transfer of sample and reagent from chambers 54, 56 to region 34 under centrifugal force nor with the mixing and analysis steps.

While a particular embodiment of the invention has been shown and described, various modifications will be apparent to those skilled in the art, and therefore it is not intended that the invention be limited to the disclosed embodiment or to details thereof and departures may be made therefrom within the spirit and scope of the invention.

What is claimed is:

1. A multicuvette rotor for use in a centrifugal analyzer, said rotor defining a circumferential array of elongated radially extending cuvettes and comprising
a one-piece body memeber of transparent material that has a planar upper surface and that defines a circumferential array of elongated cuvette recesses, and
a one-piece cover member of transparent material that has a planar lower surfce parallel to said planar upper surface of said body member with a continuous seal formed of energy director material that extends around each said cuvette recess and integrally joins said planar upper and lower surfaces to define said circumferential array of analytical cuvettes,
each said elongated cuvette including structure defining a first chamber region for receiving a first constituent and a loading port in said cover member through which said first constituent is introduced into said first chamber region,
structure defining a second chamber region for receiving a second constituent, a second loading port in said cover member through which said second costituent is introduced into said second chamber region,
divider structure between said first and second chamber regions, said divider structure having a crest portion spaced from said lower surface of said cover member so that a transfer passage between said first and second chamber regions is defined between said crest portion and said lower surface of said cover member through which said first constituent may be flowed into said second chamber region for forming a reaction product with said second constituent,
said continuous seal providing barrier structure that extends along the top of each side wall of each cuvette between said loading ports of said first and second chamber regions and fills the junction between said cover and body members so that there is no capillary channel at that junction and premature mixing of the constituents due to wicking movement of a constituent stored in one of said chamber regions to the other chamber region along that junction is inhibited, and
structure defining an analysis region adjacent the radially outer wall of said cuvette where said reaction product is subjected to analysis.

2. The rotor of claim 1 wherein said barrier structure is a ridge portion that; before sealing, is spaced from the edge of the adjacent cuvette side wall substantially the same distance as the height of said barrier ridge portion.

3. The rotor of claim 1 wherein said barrier structure extends continuously around each said cuvette recess between said planar upper and lower surfaces.

4. The rotor of claim 1 wherein said energy director material of said seal is integral with said body member.

5. The rotor of claim 1 wherein said cover member is a flat circular disc that has an optical window region, an outer circumferential array of loading ports, an inner circumferential array of loading ports, and a substantially "D" shaped central opening; and said body member has a flat upper surface, an optical window region formed in its lower surface that is aligned with the optical window region of said cover member and a circumferential array of individual cuvette recesses corresponding to said loading ports.

6. The rotor of claim 5 wherein said barrier structure is formed from an energy director ridge portion that has a sharp crest.

7. The rotor of claim 1 wherein each said cuvette recess of said rotor has a length of about three centimeters, the sidewalls of said chambers diverge, and the sidewalls of said analytical regions are parallel.

8. The rotor of claim 1 wherein said energy director material is formed from triangular energy director ridge portions that have a base width of about 0.1 millimeter, a height of about 0.1 millimeter, and are set back about 0.1 millimeter from and extend parallel to the adjacent top edge of the side walls of said cuvettes.

9. The rotor of claim 8 wherein said energy director ridge portions are integral with said body member.

10. The rotor of claim 9 wherein the sidewalls between each pair of adjacent cuvettes are formed in said body member by a solid web that has a width of less than three millimeters and that has a planar upper surface on which a pair of said energy director ridges are formed integrally therewith.

11. The rotor of claim 10 wherein said cover member is a flat circular disc that has an optical window region, an outer circumferential array of loading ports, an inner circumferential array of loading ports, and a central opening; and said body member has a flat upper surface, an optical window region formed in its lower surface that is aligned with the optical window region of said cover member and a circumferential array of individual cuvette recesses corresponding to said loading ports.

12. The rotor of claim 11 wherein each said cuvette recess of said rotor has a length of about three centimeters, the sidewalls of the chambers of each cuvette diverge, and the sidewalls of each said analytical region are parallel.

* * * * *